United States Patent [19]
Morales

[11] Patent Number: 5,920,975
[45] Date of Patent: Jul. 13, 1999

[54] STENT CRIMPING TOOL AND METHOD OF USE

[75] Inventor: Stephen A. Morales, Mountain View, Calif.

[73] Assignee: Advanced Cardiovascular Systems, Inc., Santa Clara, Calif.

[21] Appl. No.: 08/962,632

[22] Filed: Nov. 3, 1997

[51] Int. Cl.$^6$ .................................................. B23P 11/00
[52] U.S. Cl. ............................. 29/282; 29/151; 29/516; 606/1; 606/108; 606/198; 623/1
[58] Field of Search ................................ 29/516, 407.08, 29/282, 280, 715, 423, 517, 234, 235, 283, 269, 270; 606/108, 198, 1; 623/1

[56] References Cited

U.S. PATENT DOCUMENTS

| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,456,667 | 10/1995 | Ham et al. ........................ 606/198 |
| 5,476,505 | 12/1995 | Limon ................................... 623/1 |
| 5,546,646 | 8/1996 | Williams et al. . |
| 5,626,604 | 5/1997 | Cottone, Jr. . |
| 5,630,830 | 5/1997 | Verbeek . |
| 5,653,691 | 8/1997 | Rupp et al. . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |
| 5,810,838 | 9/1998 | Solar ................................ 606/108 |

FOREIGN PATENT DOCUMENTS

WO 98/14120  4/1998  WIPO .
WO 98/19633  5/1998  WIPO .

OTHER PUBLICATIONS

U.S. Patent Application Serial No. 08/795,335 filed Feb. 4, 1997.
U.S. Patent Application Serial No. 08/837,771 filed Apr. 22, 1997.
U.S. Patent Application Serial No. 08/893,936 filed Jul. 15, 1997.

Primary Examiner—Joseph M. Gorski
Assistant Examiner—John Preta
Attorney, Agent, or Firm—Fulwider Patton Lee & Utecht, LLP

[57] ABSTRACT

A stent crimping tool for firmly and uniformly crimping a stent onto a catheter. The stent crimping tool is constructed from a base having two vertically extending spaced apart supports and a coiled tension spring affixed at one end to a shaft and at the opposite end to one of the vertical supports. When a stent is loaded onto the balloon portion of a catheter, and the stent-catheter assembly is inserted into an axial space within the coiled spring, the user can rotate the shaft to twist the coiled spring thereby constricting it, and in turn the constriction of the coiled spring uniformly crimps the stent onto the balloon catheter.

23 Claims, 3 Drawing Sheets

STENT CRIMPING TOOL AND METHOD OF USE

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps. Consequently, they are unsuitable for use by physicians in a cath lab who desire to crimp the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel. The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

The present invention is directed to a crimping tool for crimping a stent onto a catheter comprising a base having a first and a second opposed vertical supports separated by a predetermined distance, a crank rotatably mounted on the second vertical support, wherein the crank includes a shaft extending towards the first vertical support and a torque transmitting member. The crimping tool further includes a cam affixed to the crank in between the first and second vertical supports, wherein the cam includes an obstruction at a circumference thereof. The invention also comprises a pawl disposed on the base and biased into engagement with the cam obstruction to prevent free rotation of the crank, and a coiled filament having an axial space, wherein the coiled filament is attached to the first vertical support and the shaft of the crank and extends between the first and second vertical supports, whereby inserting the stent mounted on the catheter into the axial space within the coiled filament and rotating the crank causes the coiled filament to constrict the stent onto the catheter.

In the preferred embodiment, the torque transmitting member is a handle which is turned by the user to twist the coiled filament. Also in the preferred embodiment, the coiled filament is a coiled tension spring. The present invention crimping tool is designed for a saphenous vein graft, carotid, or any other stent product that is released without a delivery system. It is an ideal tool for any stent that is introduced to market without such a delivery system.

All of the parts of the present invention are preferably made from nylon or a comparable polymer. The present invention stent crimping tool is intended to be used in a cath lab to accurately and repeatably crimp a stent onto a balloon catheter.

The present invention crimping tool operates as follows. A catheter with a balloon having a stent mounted thereon is inserted into the axial space within the coiled filament. The user turns the crank at the opposite end which rotates the cam and shaft of the crank. The rotating crank twists the coiled filament, which at the opposite end is affixed to the immobile first vertical support. Continued twisting of the coiled filament constricts the filament onto the stent, which stent is in turn compressed onto the balloon.

In the preferred embodiment, the coiled filament is a tension spring which when twisted has resilience tending to counter-rotate the crank. However, the ratchet mechanism formed by an obstruction, which in the preferred embodiment are unidirectional teeth at the circumference of the cam engaging the pawl, prevent the resilience in the spring from unwinding and counter-rotating the crank.

When the spring has been manually wound or twisted to the point that is has constricted to its minimum diameter, the user may force the pawl against its bias to disengage from the teeth of the cam. Once the ratchet mechanism is disengaged, the natural resilience in the spring unconstricts and unwinds in the opposite direction thus releasing the crimped stent and balloon catheter. As a result of the foregoing process, the collapsing or decreasing diameter of the constricting spring has thus homogeneously and precisely compressed the spring onto the balloon catheter.

The system is repeatable because the tool resets itself after the pawl is disengaged. The number of "clicks" by the ratchet can be counted or the number of rotations can be counted to provide accuracy and precision. Further, the stent may not be homogeneously crimped from the proximal to the distal end of the stent. A smaller diameter coil can be used if this is desired. Larger diameter coils would increase the force needed to actuate the tool, but would also increase uniformity and accuracy of the crimp.

Therefore, the present invention crimping tool is highly useful to cardiologists, for example. Such physicians are constantly concerned with proper deployment of the stent within the patient that it is desirable to have a consistently and reliably crimped stent. The present invention tool is further a time saver in that the stent crimping procedure can be performed fairly efficiently and quickly. These and other advantages of the present invention will become apparent from the following detailed description thereof when taken in conjunction with the accompanying exemplary drawings.

DETAILED DESCRIPTION OF THE PREFERRED EMBODIMENTS

Figure 1:
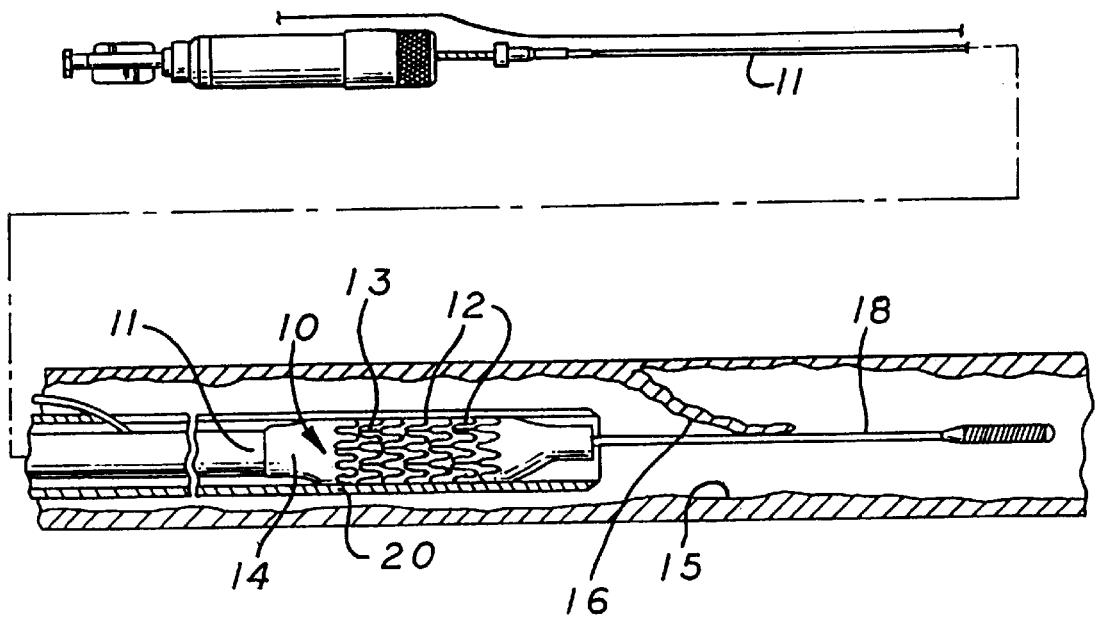
FIG. 1 is an elevational view, partially in section, depicting a stent that has been crimped onto a delivery catheter and disposed within a damaged vessel.

FIG. 1 illustrates intravascular stent 10 which is mounted onto delivery catheter 11. Stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, and other like polymers. In order for stent 10 to remain in place on balloon 14 during delivery to the site of the damage within artery 15, stent 10 is compressed onto balloon 14. This compressing step is known as crimping.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14. In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

Figure 2:
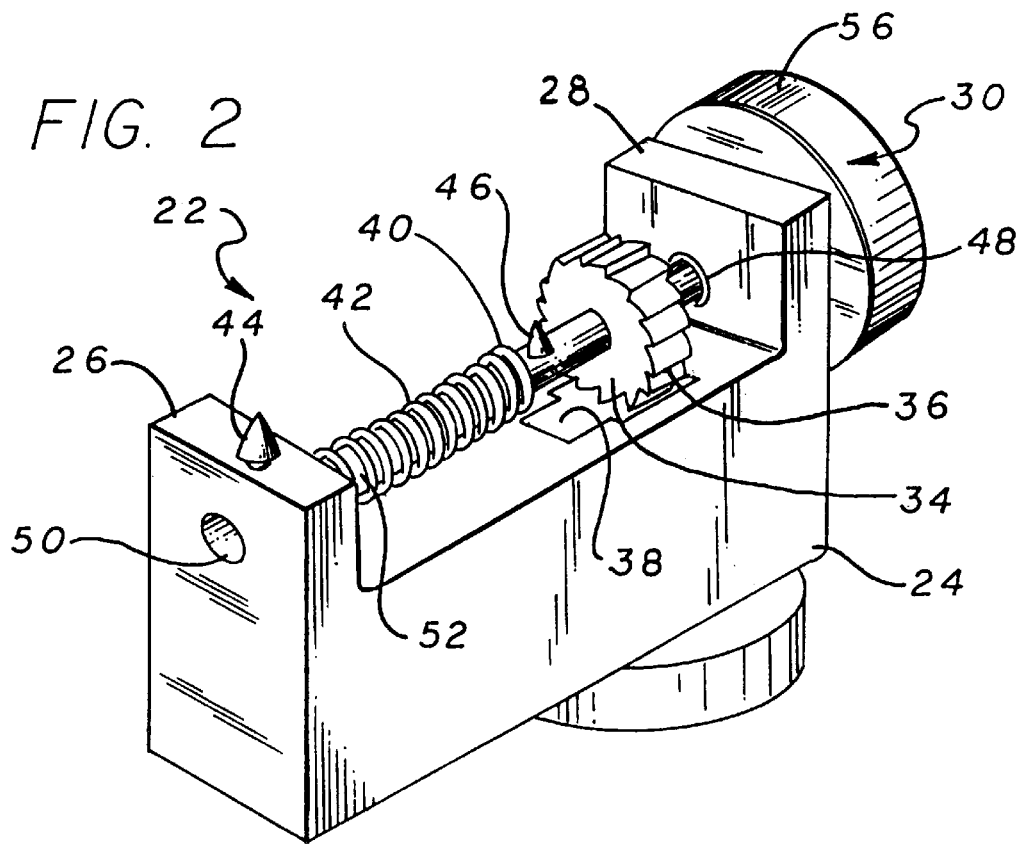
FIG. 2 is a perspective view of a preferred embodiment of the present invention stent crimping tool.

FIG. 2 provides a perspective view of a preferred embodiment stent crimping tool 22. In the preferred embodiment shown, stent crimping tool 22 has several major components comprising base 24, first vertical support 26, second vertical support 28, wherein the two vertical supports 26, 28 are spaced apart on base 24. Crank 30 has shaft 32 that rotatably passes through an opening in second vertical support 28. A cam 34 is affixed on shaft 32 whereby the cam rotates with shaft 32.

Cam 34 includes an obstruction which, in the preferred embodiment, are teeth 36 located at the circumference of cam 34 and are designed to engage pawl 38. Pawl 38 is positioned on base 24 and biased into teeth 36. Together, cam 34, teeth 36, and pawl 38 form a ratchet mechanism that permits rotation in one direction yet prevents rotation of shaft 32 in the opposite direction.

Attached to end 40 of shaft 32 is one end of coiled filament 42. The opposite end of coiled filament 42 is connected to first vertical support 26. In the preferred embodiment shown in FIG. 2, coiled filament 42 is a coiled tension spring with its ends hooked to pins 44, 46.

In the exemplary embodiment shown in FIG. 2, the present invention has fairly high extending vertical supports 26, 28, such that shaft 32 passes through second vertical support 28 rather than just resting upon it. Optional bearing 48 is located inside second vertical support 28 to minimize rotational friction between shaft 32 and second vertical support 28.

Also, through hole 50 is provided in first vertical support 26 and is in communication with axial space 52 that is defined by the coils of coiled filament 42. Thus, when stent crimping tool 22 is used, through hole 50 allows the stent-catheter assembly to be passed therethrough into axial space 52 inside coiled filament 42. In the preferred embodiment, through hole 50 is aligned with the openining housing bearing 48; although it is recognized that through hole 50 need not be aligned with the rotational axis of bearing 48.

Figure 3:
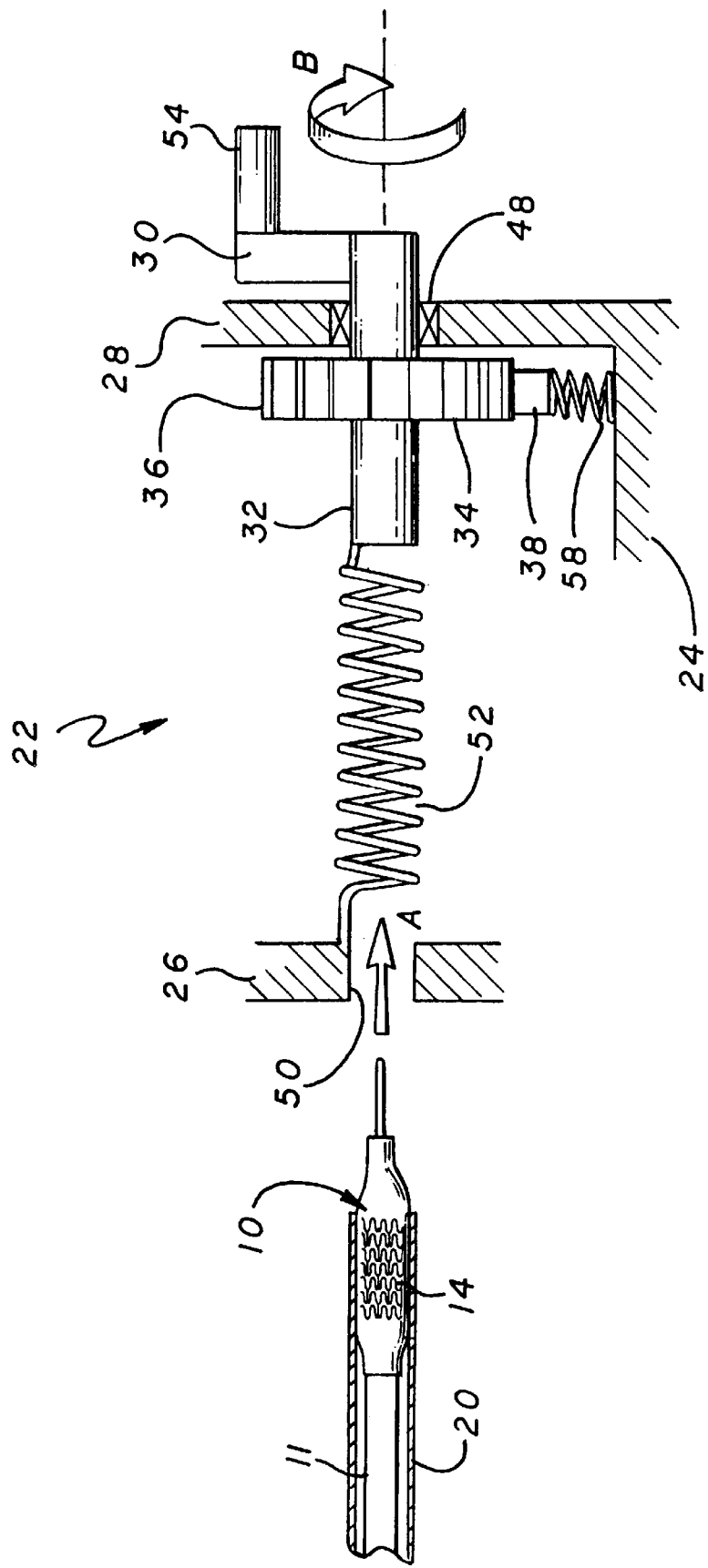
FIG. 3 is a side elevational view of the present invention drawn as a simplified schematic showing a stent mounted to a balloon catheter prior to being inserted into the axial space of the coiled filament.
Figure 4:
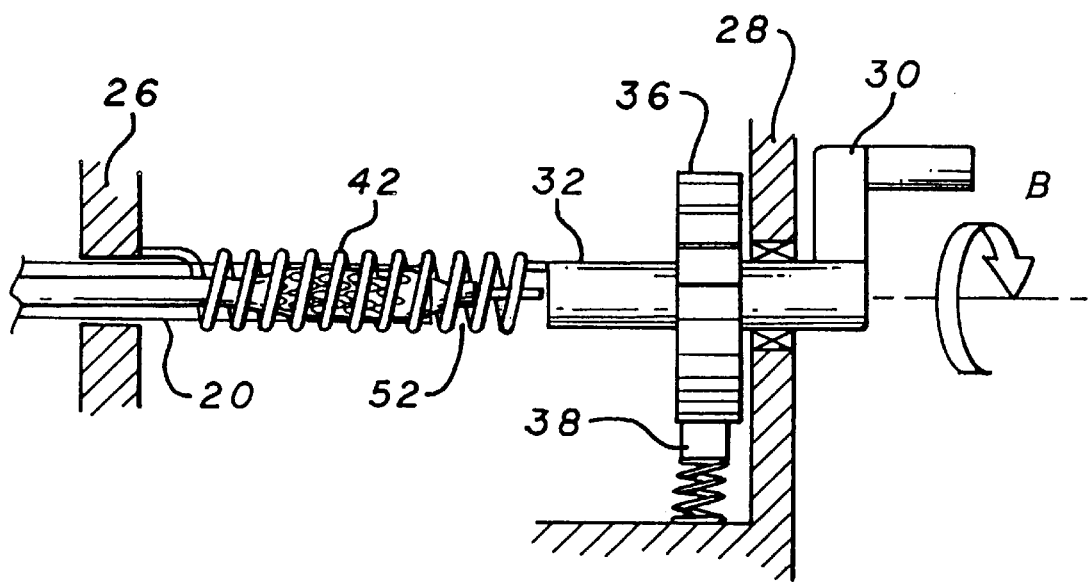
FIG. 4 is a side elevational view of the present invention following the step depicted in FIG. 3, wherein the stent-catheter assembly have been inserted into the axial space of the coiled filament.
Figure 5:
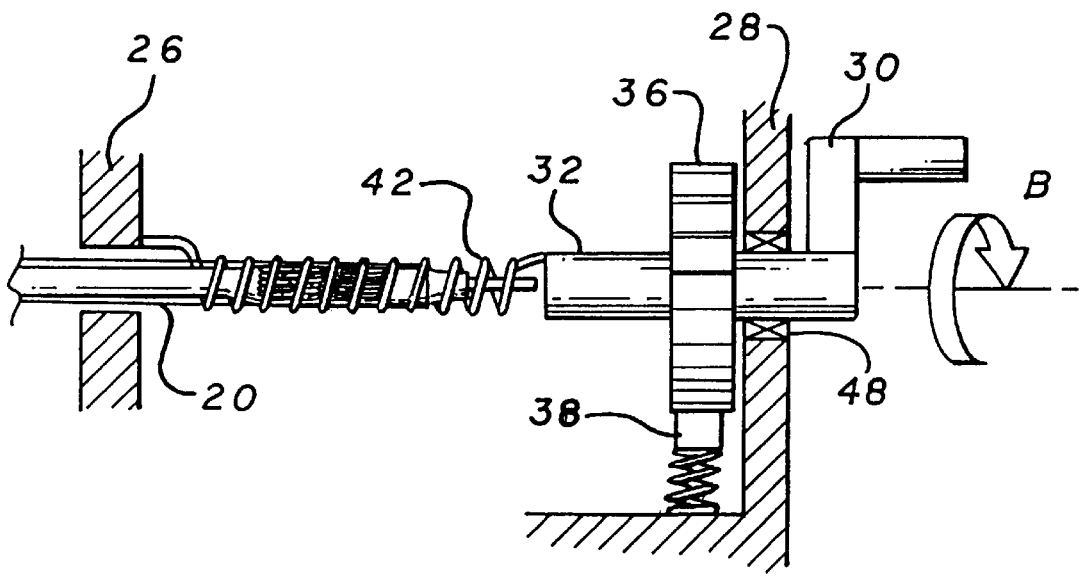
FIG. 5 is a side elevational view of the present invention following the step depicted in FIG. 4 showing rotation of the crank and constriction of the coiled filament, thus causing the stent to be crimped onto the balloon catheter.

FIGS. 3–5 are simplified schematic diagrams of a preferred embodiment of the present invention. In particular, FIG. 3 provides a side elevational view of the present invention stent crimping tool 22 just prior to insertion of the stent-catheter assembly. As seen in FIG. 3, at the left side of the drawing, stent 10 is loaded onto delivery catheter 11 so that stent 10 is overlying balloon portion 14 just prior to insertion of the assembly into through hole 50 of first vertical support 26. Arrow A shows the direction of insertion of the stent-catheter assembly into axial space 52 within coiled filament 42.

As explained above, one end of coiled filament 42 is attached to first vertical support 26 and the opposite end is anchored to shaft 32 of crank 30. In alternative embodiments of the present invention, crank 30 may have a torque transmitting member such as handle 54 as seen in FIG. 3, or textured wheel 56 as seen in FIG. 2. Other torque transmitting devices known in the art can be used as well.

FIG. 3 also shows the preferred embodiment ratcheting device that prevents counter-rotation of crank 30 during the crimping procedure. The preferred embodiment ratcheting mechanism of the present invention comprises cam 34 having teeth 36 located at a circumference thereof. Pawl 38 is biased into engagement with teeth 36 by spring 58 or the like. Pawl 38 may be operated by a lever which when turned overcomes the bias of spring 58 to disengage pawl 38 from teeth 36; conversely, releasing the lever allows the spring bias to re-engage pawl 38 to teeth 36.

In the exemplary embodiment shown in FIG. 2, pawl 38 can be made from a highly resilient material and shaped into a plate that is biased into engagement with teeth 36 of cam 34. This type of contact engagement permits rotation of shaft 32 in one direction yet resists rotation in the opposite direction due to the obstruction of pawl 38 against one or more teeth 36. Other ratcheting mechanisms known in the art can be used here as well. For example, in an alternative embodiment, the outer circumference of the cam has a rough finish and the pawl has an equally high friction finish and engages the cam under spring bias. In this alternative embodiment, friction is used to prevent rotation of the cam and shaft. The pawl would then serve as a brake against the rotating cam.

In yet another alternative embodiment, the circumference of the cam can include a detent to catch the pawl, which is biased into the cam. The profile of the detent can have an asymmetric saw-tooth shape to permit the cam to continue rotating in one direction by allowing the pawl to slide over the detent yet solidly engage the pawl if the cam rotates in the opposite direction.

FIG. 4 is a side elevational view of the present invention wherein the stent-catheter assembly has been inserted into axial space 52 within coiled filament 42. With pawl 38 disengaged from teeth 36, shaft 32 of crank 30 is free to rotate in either the clockwise or counterclockwise direction. As mentioned above, optional bearing 48 is used to lower the rotational friction between shaft 32 and second vertical support 28. Lubricants or a low friction sleeve can be used here as well.

When crank 30 is rotated in the direction of arrow B, shaft 32 rotates and begins to twist coiled filament 42, which at the opposite end is anchored to first vertical support 26. As coiled filament 42 is twisted, it constricts the stent-catheter assembly contained inside axial space 52. FIG. 5 shows this process continuing. As the user continuously turns crank 30, the constriction proceeds and the diameter of coiled filament 42 decreases steadily, thereby uniformly compressing stent 10 onto balloon portion 14 of delivery catheter 11. As shown in FIGS. 3–5, an optional sleeve or sheath 20 overlies stent 10 before and during crimping for several reasons. The sheath protects the stent until the stent is mounted over the balloon. Further, as the coiled filament compresses and reduces its diameter, the compression forces are evenly and uniformly applied over the sheath and onto the stent. After crimping, optional sheath 20 can be removed or left in place to protect the stent during intravascular delivery.

Any resilience in coiled filament 42 urging shaft 32 to counter-rotate in a direction opposite to arrow B is resisted by the ratchet mechanism. Specifically, pawl 38 in FIG. 5 is engaging teeth 36 to prevent the counter-rotation. Of course, the ratchet mechanism can be eliminated and the counter-rotation can be resisted manually by the user using force against crank 30.

Torque is applied in the direction of arrow B through crank 30 until the desired amount of crimping is achieved. The crimping process can be repeated by retracting pawl 38 from contact with teeth 36 and allowing free counter-rotation of shaft 32 to unwind coiled filament 42. At any time after coiled filament 42 has begun to unwind, crank 30 can be turned in the direction of arrow B to once again constrict coiled filament 42 onto the stent-catheter combination. This process can be repeated over and over as needed until the desired crimp is achieved. Moreover, the amount of torque applied to crank 30 can slowly increase, decrease, or remain steady in magnitude.

It is optional to keep pawl 38 fully engaged into teeth 36 during the foregoing crimping process to resist the resilience induced counter-rotation of shaft. Pawl 38 need only be disengaged from teeth 36 to permit the counter-rotation in order to release the crimped stent-catheter assembly or to restart the crimping cycle. Indeed, the crimping cycle can be repeated over and over without engagement of pawl 38 against teeth 36 insofar as the user maintains some level of torque on crank 30.

In the preferred embodiment, all parts of the present invention are made from nylon or a comparable polymer known in the art. The device is sterilized and intended to be used in the cath lab by a trained technician or cardiologist. Coiled filament 42 can be a metal tension spring, a resilient polymer ribbon (e.g. mylar) formed into a coil, or the like made from a resilient material. Preferably, the coiled filament is a coiled spring having either a flat or a round cross-section. The filament can vary in thickness or diameter as the particular application warrants.

As will be appreciated by those skilled in the art, the present invention crimping tool 22 is designed both for single use applications in a cath lab by a physician, or for multiple use applications in a sterile environment in a high volume manufacturing facility. In such a manufacturing facility where sterile conditions exist, stent crimping tool 22 can be used to repeatedly crimp stents onto balloons until the mechanism wears out. Thus, repeated uses of the present invention are contemplated for controlled, sterile environments, although single use applications are required when used by cath lab personnel.

Furthermore, the present invention crimping tool can be used with any stent that is released without a delivery system. The crimping tool may also be sold alone because its design is robust enough to undergo many uses.

What is claimed is:

1. A tool for crimping a stent onto a catheter, the tool comprising:

a base having a first support and a second support defining a space therebetween;

a crank rotatably disposed on the second support and extending toward the first support;

a coiled filament located within the space, the coiled filament having a plurality of turns defining an axial space and having a diameter, the coiled filament terminating in a first end attached to the first support and a second end attached to the crank, wherein the axial space is unobstructed along its central axis from the first end to the second end, such that when a stent and catheter are inserted into the axial space and the crank is rotated, the diameter of the axial space becomes reduced whereby the stent becomes crimped onto the catheter.

2. The crimping tool according to claim 1, wherein the crimping tool further comprises a cam affixed to the crank having an obstruction at a circumference; and a pawl disposed on the base and biased into engagement with the cam obstruction to prevent free rotation of the crank.

3. The crimping tool according to claim 2, wherein the obstruction includes a detent formed in the cam.

4. The crimping tool according to claim 2, wherein the obstruction includes a tooth.

5. The crimping tool according to claim 2, wherein the obstruction includes a frictional surface at the circumference of the cam.

6. The crimping tool according to claim 1, wherein the coiled filament includes a coiled spring.

7. The crimping tool according to claim 6, wherein the coiled spring has either a flat or a round cross-section.

8. The crimping tool according to claim 1, wherein the first support includes an opening through which the stent and catheter pass when being inserted into the axial space of the coiled filament.

9. The crimping tool according to claim 1, wherein the base includes a polymer material.

10. The crimping tool according to claim 1, wherein the coiled filament includes a flat cross-sectional shape.

11. The crimping tool according to claim 1, wherein the coiled filament includes a circular cross-sectional shape.

12. The crimping tool according to claim 1, wherein the stent is covered by a sheath so that the crimping forces of the coiled filament are evenly distributed along the stent.

13. A tool for crimping a stent on to a catheter, comprising:

a base having a first and a second opposed vertical supports separated by a predetermined distance;

a crank rotatably mounted on the second vertical support, wherein the crank includes a shaft extending toward the first vertical support and a torque transmitting member;

a cam affixed to the crank in between the first and second vertical supports, wherein the cam includes an obstruction at a circumference thereof;

a pawl disposed on the base and biased into engagement with the cam obstruction to prevent free rotation of the crank; and a coiled filament having an axial space, wherein the coiled filament is attached to the first vertical support and the shaft of the crank and extends between the first and second vertical supports;

whereby inserting the stent mounted on the catheter into the axial space within the coiled filament and rotating the crank causes the coiled filament to crimp the stent on to the catheter.

14. The crimping tool according to claim 13, wherein the torque transmitting member includes a handle.

15. The crimping tool according to claim 13, wherein the torque transmitting member includes a wheel.

16. The crimping tool according to claim 13, wherein the first and second vertical supports include respective first and second openings, and wherein the shaft of the crank passes through the second opening.

17. The crimping tool according to claim 16, wherein the second opening includes a bearing.

18. A method for crimping a stent on to a catheter, comprising the steps of:

providing a base having at least a first and second spaced apart supports;

providing a crank rotatably disposed on the second support and extending toward the first support;

stretching a coiled filament having an axial space from the first support to the crank;

affixing a cam having an obstruction at a circumference to the crank;

biasing a pawl, disposed on the base, into engagement with the cam obstruction to prevent free rotation of the cam;

inserting the stent and catheter into the axial space of the coiled filament; and rotating the crank to overcome the bias of the pawl against the cam to twist the coiled filament;

whereby twisting the coiled filament reduces the diameter of the axial space thereby crimping the stent onto the catheter.

19. The method according to claim 18, wherein the step of stretching the coiled filament includes a step of providing a coiled spring.

20. The method according to claim 18, wherein the method further comprises the steps disengaging the pawl from the cam obstruction and repeatedly rotating and releasing the crank.

21. The method according to claim 18, wherein the method further comprises the steps of rotating the crank, disengaging the pawl from the cam obstruction, engaging the pawl against the cam obstruction, and rotating the crank.

22. The method according to claim 18, wherein the method further comprises the step of applying increasing torque when rotating the crank.

23. The method according to claim 18, wherein the method further includes covering the stent with a sheath prior to the step of inserting the stent and catheter into the axial space of the coiled filament so that as the coiled filament reduces the axial space, the forces imparted will be evenly and uniformly distributed onto the stent to crimp it onto the catheter.

* * * * *

UNITED STATES PATENT AND TRADEMARK OFFICE
CERTIFICATE OF CORRECTION

PATENT NO. : 5,920,975
DATED : Jul. 13, 1999
INVENTOR(S) : Stephen A. Morales

It is certified that error appears in the above-identified patent and that said Letters Patent is hereby corrected as shown below:

Title page under References Cited, "U.S. PATENT DOCUMENTS", add --5,836,952  11/1998  Davis, et at.--.

Title page under References Cited, OTHER PUBLICATIONS, add, --The ExTraordinary Stent, C.R. Bard Brochure, (undated).--.

Signed and Sealed this

Eleventh Day of January, 2000

Attest:

Q. TODD DICKINSON

*Attesting Officer*

*Acting Commissioner of Patents and Trademarks*